United States Patent
Vitzthum et al.

(10) Patent No.: US 11,226,338 B2
(45) Date of Patent: Jan. 18, 2022

(54) COOMASSIE BRILLIANT BLUE ASSAY WITH IMPROVED SENSITIVITY

(71) Applicant: Siemens Healthcare Diagnostics Inc., Tarrytown, NY (US)

(72) Inventors: Frank Vitzthum, Biedenkopf (DE); Herbert Schwarz, Lohra (DE); Anja Haude-Barten, Marburg (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 471 days.

(21) Appl. No.: 16/321,709

(22) PCT Filed: Aug. 10, 2017

(86) PCT No.: PCT/US2017/046227
§ 371 (c)(1),
(2) Date: Jan. 29, 2019

(87) PCT Pub. No.: WO2018/034926
PCT Pub. Date: Feb. 22, 2018

(65) Prior Publication Data
US 2021/0278412 A1 Sep. 9, 2021

Related U.S. Application Data

(60) Provisional application No. 62/376,047, filed on Aug. 17, 2016.

(51) Int. Cl.
*G01N 33/68* (2006.01)
*G01N 33/48* (2006.01)

(52) U.S. Cl.
CPC ......... *G01N 33/6839* (2013.01); *G01N 33/48* (2013.01)

(58) Field of Classification Search
CPC .............. G01N 33/68; G01N 33/6803; G01N 33/6827; G01N 33/6839; G01N 33/48
USPC ....... 436/63, 86, 164, 166; 422/82.05, 82.09
See application file for complete search history.

(56) References Cited

U.S. PATENT DOCUMENTS

| | | | |
|---|---|---|---|
| 4,023,933 A | 5/1977 | Bradford et al. | |
| 4,219,337 A * | 8/1980 | Grossberg | G01N 33/6839 422/430 |
| 4,239,495 A * | 12/1980 | Gindler | G01N 33/6839 436/86 |
| 5,273,906 A * | 12/1993 | Shultz | C07D 311/82 204/462 |
| 5,693,291 A | 12/1997 | Strobel et al. | |
| 5,908,787 A * | 6/1999 | Cast | G01N 33/683 436/86 |
| 6,057,160 A | 5/2000 | Silber et al. | |
| 6,241,946 B1 | 6/2001 | Bickar | |
| 6,319,720 B1 * | 11/2001 | Wondrak | G01N 1/30 436/15 |
| 6,338,967 B1 * | 1/2002 | Bickar | G01N 33/6839 436/15 |
| 9,034,652 B2 * | 5/2015 | Belisle | G01N 33/6839 436/86 |
| 2009/0298185 A1 | 12/2009 | Jones et al. | |
| 2015/0219564 A1 | 8/2015 | Vilzlhum et al. | |

FOREIGN PATENT DOCUMENTS

| | | |
|---|---|---|
| EP | 2016421 A1 | 1/2009 |
| EP | 2295979 A2 | 3/2011 |

OTHER PUBLICATIONS

Zor et al. Analytical Biochemistry, vol. 236, pp. 302-308, 1996.*
European Search Report and Written Opinion of European Application No. 17841885.1 dated May 21, 2019.
International Search Report and Written Opinion of International Application No. PCT/US2017/046227 dated Oct. 24, 2017.
Ernst et al, "Linearization of the Bradford Protein Assay", Apr. 12, 2010, J Vis Exp., vol. 38, pp. 1-8.

* cited by examiner

*Primary Examiner* — Maureen Wallenhorst

(57) ABSTRACT

Methods for detection and quantitative measurement of proteins with a Coomassie Brilliant Blue Assay with improved sensitivity and maintaining high linearity over a broad measuring range are provided herein. In particular, a method of detecting a protein in a protein-containing sample is provided. The method includes providing a sample including a protein, a reagent including Coomassie Brilliant Blue and having a pH between 0.85 and 1.1, combining the sample and the reagent, and determining absorption at first and second wavelength to determine the amount of protein in the sample. The ratio of the absorption value at the first wavelength between about 580 to 620 nm to the absorption value at the second wavelength between about 520 to 370 nm is used in the spectral photometric determination of the amount of protein.

11 Claims, 2 Drawing Sheets

COOMASSIE BRILLIANT BLUE ASSAY WITH IMPROVED SENSITIVITY

This application claims priority to U.S. Provisional Application No. 62/376,047, filed Aug. 17, 2016, the disclosure of which is hereby incorporated by reference in its entirety.

FIELD OF THE INVENTION

The present invention relates to the detection and quantitative measurement of proteins with the Coomassie Brilliant Blue Assay with improved sensitivity.

BACKGROUND OF THE INVENTION

Several methods are known for detecting the presence of protein in samples. These include the classical Lowry (Lowry, Oh. H., Rosebrough, N. J., Farr, A. L., and Randall R. J. (1951), J. Biol. Chem. 193, 265-275.) and Biuret (Mokrasch, L. C., and McGilvery, R. W. (1956) J. Biol. Chem. 221, 909-917) methods, which suffer from interference by many substances commonly present in protein-containing solutions. Dye/protein complex formation is also utilized for staining of proteins in gels used in electrophoresis. For example, the dye Coomassie Brilliant Blue G-250 in perchloric acid solution has been so used (Reisner, A. H. et al (1975) Anal. Biochem. 64, 509-516). However, these techniques involve precipitation of the colored protein/dye complex and are inapplicable to sensitive quantitative analysis of protein-containing solutions where spectrophotometric means are generally used for measurements.

A more sensitive and rapid method for quantitative analysis of small amounts (μg) of protein comprises the dye Coomassie Brilliant Blue (CBB) and an acid having a pKa-value from 1 to 2 in the presence of an alcohol such as ethanol (U.S. Pat. No. 4,023,933; Bradford MM. A rapid and sensitive method for the quantitation of microgram quantities of protein utilizing the principle of protein-dye binding. *Anal. Biochem.* 1976; 72; 248-254).

In order to improve the sensitivity detergents such as Triton® X-100 were successfully added to the CBB Assay (Friedenauer S, Berlet H H. Sensitivity and variability of the Bradford protein assay in the presence of detergents. *Anal Biochem* 1989; 178; 263-268). Zor and Selinger improved the linearity and sensitivity by using the ratio and/or the difference of/between the absorption values at 590 nm and 450 nm (Zor T, Selinger Z. Linearization of the Bradford protein assay increases its sensitivity: theoretical and experimental studies. *Anal. Biochem.* 1996; 236; 302-308).

Linearity is a measuring curve characteristic. Measuring curve characteristics refer to the dependence of the signal and the concentration of protein, whereas the signal can also be a result derived from signals through algorithms, e.g. a difference or ratio in signals like absorption values. Ideally, the dependence shows high linearity over a wide dynamic range, i.e. in the same setting the concentration range that can be measured and shows a linear correlation is covering low and high concentrations.

A measure for linearity is the correlation coefficient or a low error of the slope of the curve when a linear regression is performed. The closer the coefficient of correlation is to the value of 1, the better the linear correlation.

The slope can also be an indicator of the sensitivity. The higher the slope value, the better the differentiation between two data points, when the error or correlation coefficient is comparable.

In order to accurately compare measuring curve characteristics and including the sensitivity of a method, one can directly compared the state of the art set up outlined in the literature, with new settings, and compare parameters like correlation coefficients, curve slopes and their errors to determine whether a new method has a higher sensitivity by a higher slope value while maintaining high correlation coefficients and low error of the slope value.

The Problem Underlying the Invention

It is desirable to further improve measuring curve characteristics, i.e. to further improve linearity over an as wide as possible concentration range or by higher slope values with low error. Higher slope values increase sensitivity, because there is better separation between data points, when the error is comparable. By increasing the sensitivity, it is possible to differentiate or determine protein concentrations or amounts that were not detectable before by the method or only with increased effort. E.g., if the protein concentration of a solution is not high enough to be detected with sufficient precision, the solution needs to be condensed. E.g., condensing can be performed via precipitation and resuspension in a smaller volume, by evaporation or ultrafiltration. However, these processes increase variation, error and can introduce bias and decrease trueness and precision of measurement. Alternatively, a different, more sensitive method like the use of fluorescent dyes using the respective equipment can also be applied. This increases the effort, costs, and time to achieve results.

Increasing linearity solves the problem of bias when a calibration curve is based on linear regression. With higher linearity the accuracy increases, when linear regression is used for value assignment. Typically a linear regression is used for simplicity. The higher the linearity of the correlation of the protein concentration to the signal, the higher the trueness of measurement, when a linear regression is used for calibration and value assignment.

Higher precision and trueness of measurement allow for more accurate conclusions to be drawn from analytical results and making the right decision, e.g. using the right protein concentration in a production process, which can save significant amounts of money in particular when large scales are applied.

BRIEF SUMMARY OF THE INVENTION

Surprisingly the combination of using a CBB reagent with an increased pH-value and the use of the ratio of the absorption value at about 595 nm to the one at about 470 nm increased the slope of the curve significantly and thereby the sensitivity. Using the absorption ratio 595/470 nm, the highest slope value and consequently the highest sensitivity was observed at a pH-value of 0.99. This is 1.6 fold higher, if comparted to the slope value observed at the pH-value of 0.77, which is the state of the art pH-value of the reagent.

DETAILED DESCRIPTION OF THE INVENTION

The Conventional Assay

Figure 1:
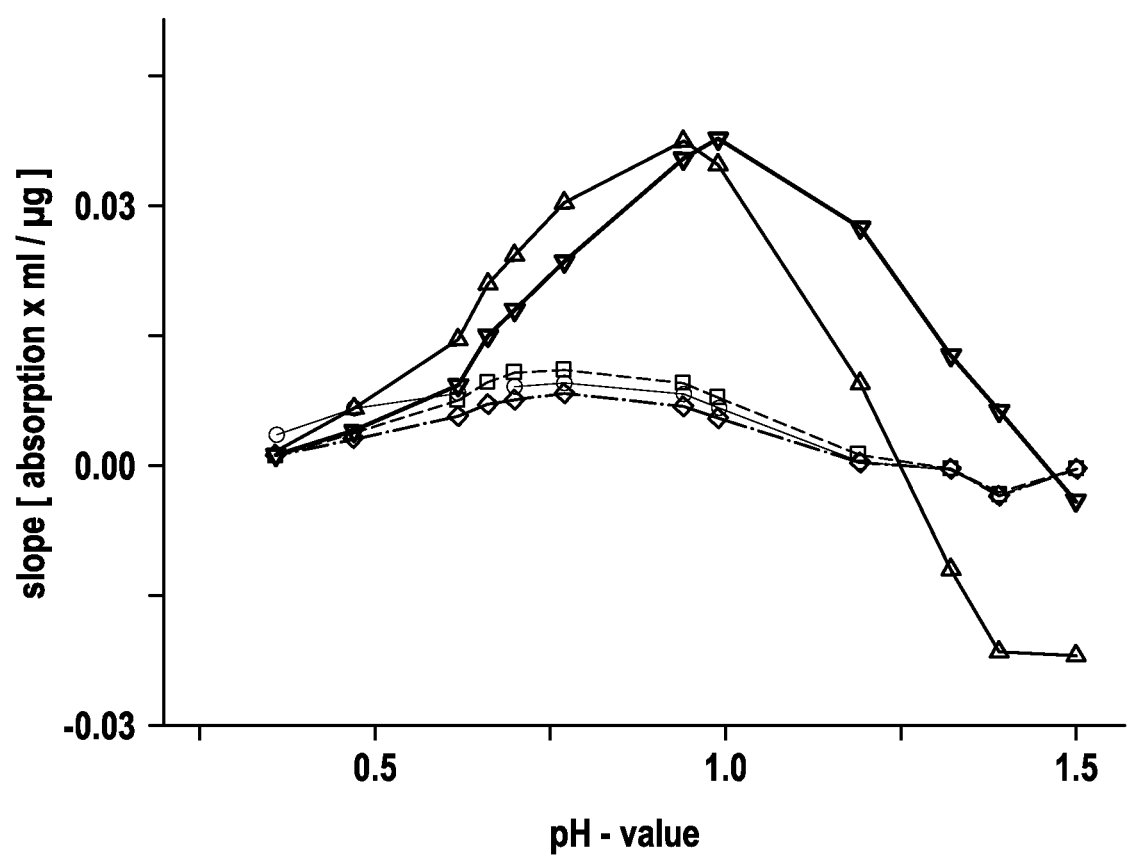
FIG. 1 shows the dependency of the slope of BSA calibration curves from the pH-value of the Coomassie Brilliant Blue reagent and the measuring system used.

The active color-changing ingredient in the reagent of the conventional CBB-Assay is the dye Coomassie Brilliant Blue G-250 (C.I. 42655, CAS-#6104-58-1).

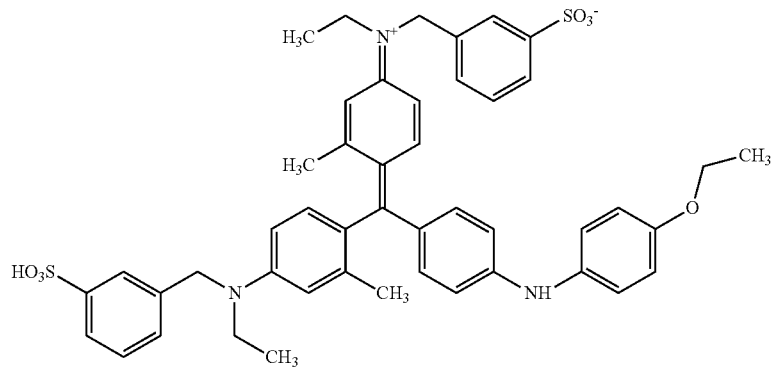

Coomassie Brilliant Blue G-250, C.I. 42655, CAS-# 6104-58-1

The G-250 dye is used in an appropriate acid medium. In the conventional assay the acid ingredient must have a pKa-value of from 0 to 4, preferably from 1 to 2, and the resultant dye-containing solution should have a pH-value of from −1 to 1, preferably from −0.5 to 0.5. Highly ionized acids such as perchloric acid, hydrochloric acid and sulfuric acid cannot be used in the reagent. Suitable acids include phosphoric acid and other acids with a pKa-value from 1-2 which do not result in protein precipitation. Typical candidates include periodic, phosphorous, selenic, sulfurous, maleic, oxalic, dichloroacetic acids and the like. Phosphoric acid is especially preferred.

The dye and the acid may be dissolved in any aqueous medium that does not contain surfactants, detergents, or exceedingly strong alkali; it is preferably dissolved in water. The final concentration of the G-250 dye in the reagent should be from 0.001 to 0.1% (w/v), preferably from 0.005 to 0.05% (w/v); while that of the acid should be from 4 to 12% (w/v), preferably 7.5 to 9.5% (w/v). The order of addition of the dye and the acid is immaterial and both may be added directly to the aqueous medium or may be added to separate portions of the medium and thereafter mixed.

With the addition of an alcohol a doubling in sensitivity of the reagent is achieved. Suitable alcohols include methanol, ethanol and propanol. Other appropriate alcohols are those with good water solubility which show no behavior as detergents. Especially preferred is ethanol. The concentration of the alcohol is preferably from 0.1% to 10% (w/v) more preferably from 4 to 5% (w/v) for the dye and acid concentrations given above.

The assay method involves addition of the reagent to a protein-containing sample, or vice versa. Detection of the protein is effected by monitoring of the increase in absorbance at 595 nm due to formation of the dye/protein complex, using conventional instrumentation such as a Bausch and Lomb Spectronic 200 UV Spectrophotometer or any colorimeter capable of measuring radiation of a wavelength in the range of from 570 to 620 nm. The amount of protein is determined by comparison with calibrators to establish a calibration curve under the same conditions as the samples to be tested. The results are highly reproducible and accurate. Temperature is not critical. Typically, the assay is carried out at room temperature.

In the above described conventional form the reagent is capable of detecting amounts of protein as small as from 0.5 to 1 μg in 0.1 ml of sample. The time required for such determinations is less than about 2 minutes per sample. The system has been automated using 0.005 ml of sample and 0.250 ml of reagent per assay. Standard deviation on 135 samples has been determined to be ±0.6% of the mean.

Typical applications of the reagent and method include detection of protein in urine, serum, cerebrospinal fluid, foods, and any other biologically derived fluid or extract.

The Assay According to the Invention

In the conventional assay the wavelength of 595 nm for determination of the absorbance is selected, because the difference of the absorption between the two forms of the CBB dye—the free and the protein bound—is at a maximum at about 595 nm. One hypothesis is that the dye binds to proteins via van-der-Waals and hydrophobe interaction, specifically interactions with basic amino acids like arginine, lysine, histidine. The number of dye molecules is said to correlate with the number of positive charges on the proteins. Typically, free amino acids, peptides and low molecular proteins (below 3000 g/mole) do not react with CBB.

Apart from other influences on the spectral properties upon binding of the dyes to proteins, it is assumed that the change in the spectral properties is in particular due to a change in the protolytic equilibrium of the dyes (Kaler GV, Gavrilov VB. A shift in protolytic equilibrium upon binding of protein-sensing dyes to protein is the basic mechanism of absorbance response Mol. Biol. 1994; 28; 140-143). This acid-base reaction comes along with a significant change in spectrophotometric properties.

In highly acidic aqueous medium CBB takes the diprotonated cationic form ($AH_2^+$). CBB is thus able to deprotonate two protons. The pK-values of these two deprotonation reactions are close to one another. During this reaction CBB is deprotonated in two steps, first at pH 0.3 to a red (470 nm) colored cation ($AH_2^+$) via a green (650 nm) electrically neutral substance (AH) to a negatively charged blue (595 nm) anion (A−) at pH 1.3.

According to the prior art the CBB reagent is typically used at a pH-value of between −0.5 and 0.5 and measured at a wavelength of about 595 nm. FIG. 1 shows the dependency of the slope of BSA calibration curves from the pH-value of the CBB reagent and the measuring system used, i.e. whether a single wavelength, a difference of wavelengths or a ratio of wavelengths has been used. The slope of the curve is an indication of the sensitivity of the method. The higher the slope value, the higher the sensitivity. It is evident from FIG. 1 that the ratio of the absorption at 595 nm and the absorption at 400 or 470 nm yields in a significantly higher slope value and thus higher sensitivity than the corresponding differences or measurement at 595 nm alone.

Thus, surprisingly, the sensitivity is not only dependent on the pH-value of the reagent used or only on the signal used. It is a combination of both and there is a discrete optimum. So, there is an optimal pH-value range for the signal used, i.e. whether a single wavelength (595 nm), a difference of wavelengths or a ratio of wavelengths is used. The pH-optimum of the sensitivity for the ratio is between about pH 0.85 and pH 1.1, in particular between pH 0.90 and pH 1.05. In contrast thereto, according to FIG. 1 the pH-optimum for the difference or the single determination at 595 nm is at about 0.77. This pH-value is typically used and, for example, corresponds to the pH-value of the commercial CBB Base reagent.

In contrast to the prior art, the present invention denotes a reagent with a pH-value of 0.85 to 1.1 preferably 0.90 to 1.05, and particularly preferably of 0, 95 to 1.00 to obtain optimal measuring curve characteristics in order to increase the sensitivity and maintain high linearity over a broad measuring range of the protein detection by CBB. In addition, a method is used in which a ratio of the absorption at about the maximum at about 595 nm, i.e. at 580-620 nm, in particular between 590 and 600 nm and a secondary wavelength of between 520 and 370 nm, preferably between 500 and 380 nm, most preferably between 470 and 400 nm, and even more preferred at about 470 nm is used.

The active color-changing compound in the reagent of the CBB-Assay of the present invention is the dye Coomassie Brilliant Blue G-250 (chemical formula as depicted above). The G-250 dye is used in an appropriate acid medium so that the solution has a pH-value of from 0.85 to 1.1 preferably from 0.90 to 1.05, and particularly preferably from 0.95 to 1.00. Suitable acids include phosphoric acid and other acids with a pKa-value from 1-2, which do not result in protein precipitation. Typical candidates include periodic, phosphorous, selenic, sulfurous, maleic, oxalic, dichloroacetic acids and the like. Phosphoric acid is especially preferred.

The dye and the acid may be dissolved in any aqueous medium that may or may not contain surfactants and/or detergents; it is preferably dissolved in water. The final concentration of the G-250 dye in the reagent should be from 0.001 to 0.1% (w/v), preferably from 0.005 to 0.05% (w/v); while that of the acid should be from 4 to 12% (w/v), preferably 7.5 to 9.5% (w/v). The order of addition of the dye and the acid is immaterial and both may be added directly to the aqueous medium or may be added to separate portions of the medium and thereafter mixed.

The addition of an alcohol may even further increase the sensitivity of the reagent. Suitable alcohols include methanol, ethanol and propanol. Other appropriate alcohols are those with good water. Especially preferred is ethanol. The concentration of the alcohol is preferably from 0.1% to 10% (w/v) more preferably from 4 to 5% (w/v) for the dye and acid concentrations given above.

The assay method involves addition of the reagent to a protein-containing sample, or vice versa. Detection of the protein is effected by monitoring of the absorbance at a first wavelength between 580-620 nm, in particular between 590 and 600 nm and most preferred at about 595 nm and at a second wavelength between 520 and 370, preferably between 500 and 380 nm, more preferably between 470 and 400 nm, and even more preferred at about 470 nm, using conventional instrumentation such as the spectrophotometer Spectra Max Plus from Molecular Devices or any colorimeter capable of measuring radiation of a wavelength in the range of from 370 to 620 nm. The ratio is then formed of the absorbance at the first wavelength to the absorbance at the second wavelength. The amount of protein is determined by comparison of the obtained ratio with the ratios of calibration curves (calibration curves; obtained with proteins at known concentrations). The results are highly reproducible and accurate. Temperature is not critical. Typically, the assay is carried out at room temperature.

Typical applications of the reagent and method according to the invention include detection of protein in urine, serum, cerebrospinal fluid, foods, and any other biologically derived fluid or extract.

Having generally described the invention, a more complete understanding can be obtained by reference to certain specific examples, which are included for purposes of illustration only and are not intended to be limiting unless otherwise specified.

EXAMPLES

For the experimental trials, the following materials were used:
- Bovine serum albumin (BSA; A7030-50G; Batch 124K0597) from Sigma (Taufkirchen, Germany);
- Hepes (catalog number 441475K, Lot K35477084 647) from BDH Chemical (Poole, UK);
- Triton® X-100 (Catalog No. 1.08603.1000) and
- Glycine (catalog number 1.04201.1000; Lot K34245201515) both from Merck (Darmstadt, Germany)
- CBB Base Reagent concentrate (Protein Assay; Dye Reagent Concentrate) (Cat. No. 500-0006; Lot No 105 341), also called Bradford reagent from Bio-Rad (Munich, Germany);
- PS microplates 96 Well (Catalog No. 655 101; Lot 03 26 01 03 F-form) from Greiner Bio-One (Frickenhausen, Germany);
- Spectrophotometer Spectra Max Plus from Molecular Devices.

An aqueous BSA base-solution with a concentration of 100 µg/mL BSA was prepared. BSA-calibration samples of 100, 80, 60, 40, 20 and 10 µg/mL were prepared from the base-solution by corresponding dilution with water. The calibration sample without BSA was water. The Bradford reagent was prepared by a 1+4 (v/v) dilution of the concentrate with water; typically 10 ml reagent and 40 µl of water. Various samples of the reagent were prepared at different pH-values. pH-values were adjusted by adding concentrated 5 N HCl- or 5 N NaOH-solutions before the final dilution of the Bradford reagent of 1+4. When the pH-value was set the final dilution was achieved by adding water and the pH-was determined again. The pH-value of the solution without adjustment of the pH-value was 0.77. 60 µl of sample was placed in a well of a multi-well-plate followed by the addition of 240 µl of Bradford reagent. After about 10 minutes incubation time at room temperature (23° C.), the well was analyzed in the spectrophotometer.

FIG. 1 shows the BSA calibration series, which were taken at different wavelengths (400, 470 and 595 nm) and different pH-values. In FIG. 1 the following symbols having the meanings as described were used: ◇ absorption at 595 nm, ○ absorption difference at 595 nm and 400 nm, □ absorption difference at 595 nm and 470 nm, △ absorption ratio at 595 nm and 400 nm; ∇ absorption ratio at 595 nm and 470 nm.

Figure 2:
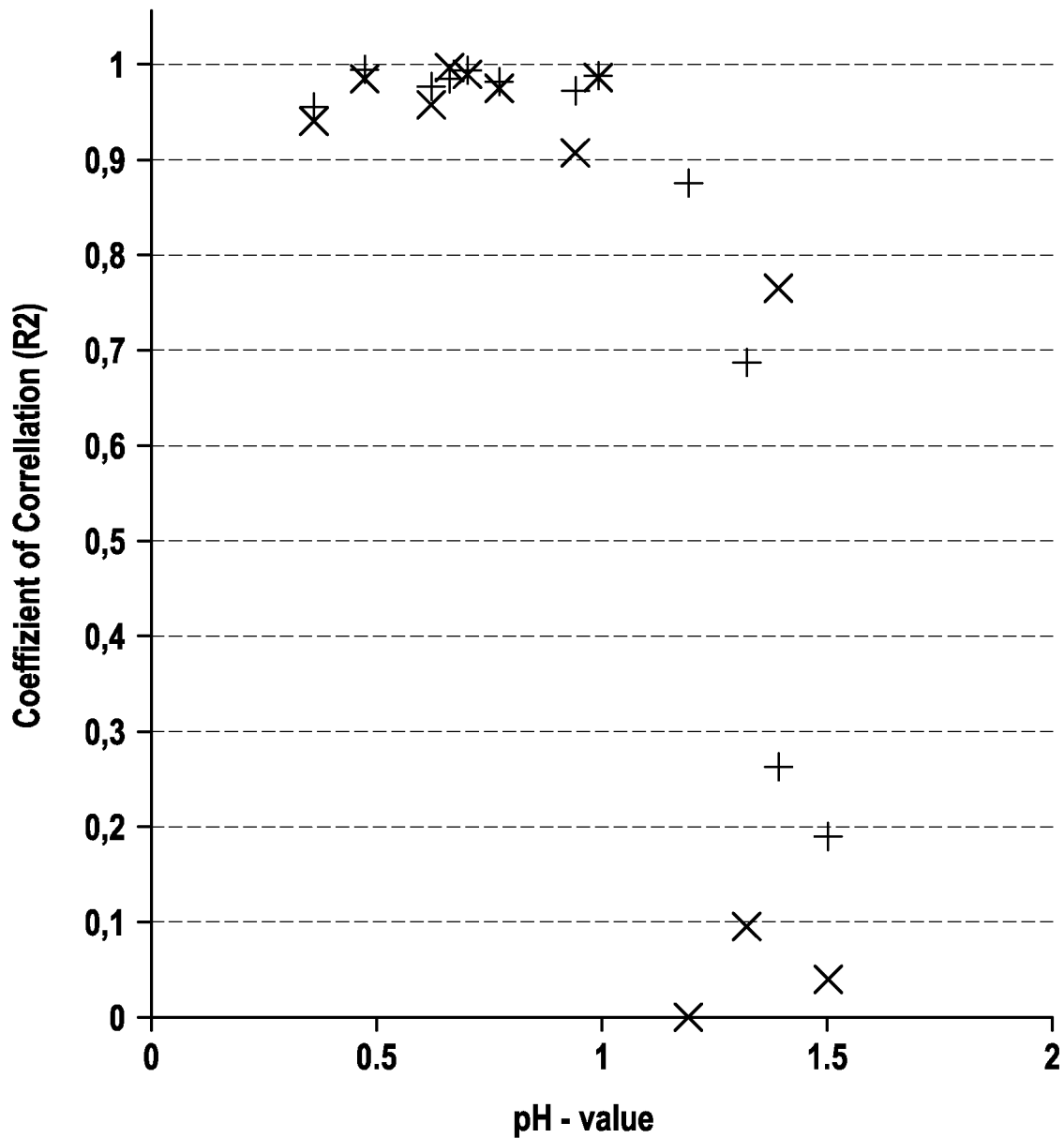
FIG. 2 shows the dependence of the coefficients of correlation ($R2$ values) depending on the pH-value of the reagent and the absorption at 595 nm (x) or the absorption ratio of 595 nm over 470 nm (+).

FIG. 2 shows the dependence of the coefficients of correlation (R2 values) depending on the pH-value of the reagent and the absorption at 595 nm (x) or the absorption ratio of 595 nm over 470 nm (+). The coefficients of correlation show that the linearity is high and maintained up to pH-values of around 1.1.

Table 1 shows the respective values. The units of the slopes and errors are in absorption x mL/µg and have been determined using the software Origin Lab Version 7. The highest slope and consequently the highest sensitivity is at the pH-value of 0.99 using the absorption ratio 595/470 nm. This is 4.7 fold higher if compared to the absorption measurement only at 595 nm at the typical pH-value of 0.77. It is 1.6 fold higher if comparted to the absorption ratio 595/470 at the typical pH-value of 0.77.

TABLE 1

| pH-value | 595-470 nm | | 595-400 nm | | 595/400 nm | | 595/470 nm | | 595 nm | |
|---|---|---|---|---|---|---|---|---|---|---|
| | Slope | Error | Slope | Error | Slope | Error | Slope | Error | Slope | Error |
| 1.5 | −0.0007 | 0.0013 | −0.0009 | 0.0013 | −0.0222 | 0.0035 | −0.0045 | 0.0038 | −0.0007 | 0.0014 |
| 1.39 | −0.0034 | 0.0008 | −0.0037 | 0.0008 | −0.0218 | 0.0037 | 0.0060 | 0.0041 | −0.0038 | 0.0009 |
| 1.32 | −0.0005 | 0.0009 | −0.0009 | 0.0009 | −0.0124 | 0.0036 | 0.0124 | 0.0034 | −0.0008 | 0.0010 |
| 1.19 | 0.0009 | 0.0003 | 0.0003 | 0.0003 | 0.0091 | 0.0036 | 0.0271 | 0.0042 | 0.0000 | 0.0003 |
| 0.99 | 0.0075 | 0.0003 | 0.0063 | 0.0003 | 0.0343 | 0.0010 | 0.0374 | 0.0018 | 0.0051 | 0.0003 |
| 0.94 | 0.0092 | 0.0007 | 0.0079 | 0.0006 | 0.0369 | 0.0018 | 0.0352 | 0.0025 | 0.0065 | 0.0005 |
| 0.77 | 0.0107 | 0.0008 | 0.0092 | 0.0005 | 0.0298 | 0.0017 | 0.0233 | 0.0014 | 0.0080 | 0.0005 |
| 0.7 | 0.0105 | 0.0005 | 0.0087 | 0.0004 | 0.0239 | 0.0010 | 0.0176 | 0.0007 | 0.0072 | 0.0003 |
| 0.66 | 0.0096 | 0.0003 | −0.1159 | 0.0133 | 0.0205 | 0.0009 | 0.0147 | 0.0008 | 0.0069 | 0.0002 |
| 0.62 | 0.0073 | 0.0004 | 0.0081 | 0.0002 | 0.0141 | 0.0009 | 0.0091 | 0.0006 | 0.0053 | 0.0005 |
| 0.47 | 0.0035 | 0.0001 | 0.0063 | 0.0004 | 0.0062 | 0.0002 | 0.0039 | 0.0001 | 0.0028 | 0.0002 |
| 0.36 | 0.0008 | 0.0003 | 0.0031 | 0.0001 | 0.0015 | 0.0001 | 0.0010 | 0.0001 | 0.0009 | 0.0001 |

Thus the invention comprises the following embodiments:
1. Method of detecting a protein in a protein-containing sample, comprising
   providing a sample comprising a protein
   providing a reagent comprising Coomassie Brilliant Blue
   combining the sample and the reagent
   determine of the absorption to determine the amount of protein in the sample wherein
   the pH-value of the reagent is between pH 0.85 and pH 1.1, and
   the ratio of the absorption value at a first wavelength of between about 580 to 620 nm to the one at a second wavelength of between about 520 to 370 nm is used in the photometric determination of the amount of protein.
2. The Method of embodiment 1, wherein the pH-value is between about pH 0.90 and pH 1.05.
3. The Method of embodiment 1, wherein the pH-value is between about pH 0.95 and pH 1.00.
4. The Method of embodiment 1, 2 or 3, wherein first wavelength is between 590 and 600 nm and the second wavelength is between 470 and 400 nm.
5. The Method of embodiment 1, 2 or 3, wherein first wavelength is about 595 nm and the second wavelength is about 470 nm.
6. The Method of one of embodiments 1-5, wherein the Coomassie Brilliant Blue is Coomassie Brilliant Blue G-250 (CI 42655, CAS-#6104-58-1) of the formula:

7. The Method of claim embodiment 6, wherein the Coomassie Brilliant Blue G-250 dye is used in an acid medium wherein the acid has a pKa-value from 1-2.
8. The Method of one of embodiments 1-7, wherein the concentration of Coomassie Brilliant Blue in the reagent is from 0.001% to 0.1% (w/v).
9. The Method of one of embodiments 1-8, wherein an alcohol is added to the reagent.
10. The Method of embodiment 9, wherein the alcohol is selected from one or more alcohols of the group consisting of methanol, ethanol and propanol.
11. The Method of embodiment 9 or 10, wherein the alcohol concentration in the reagent is from 0.1% to 10% (w/v).
12. Use of the Method of one of embodiments 1-11, for the detection of protein in urine, serum, cerebrospinal fluid, foods, and any other biologically derived fluid or extract.
13. A reagent comprising Coomassie Brilliant Blue G-250 (CI 42655, CAS-#6104-58-1) and an acid with a pKa-value from 1-2.
14. The reagent of embodiment 13, further comprising an alcohol.
15. The reagent of embodiment 14, wherein the alcohol is selected from one or more alcohols of the group consisting of methanol, ethanol and propanol.

The invention claimed is:
1. A method of detecting an amount of a protein in a protein-containing sample, comprising

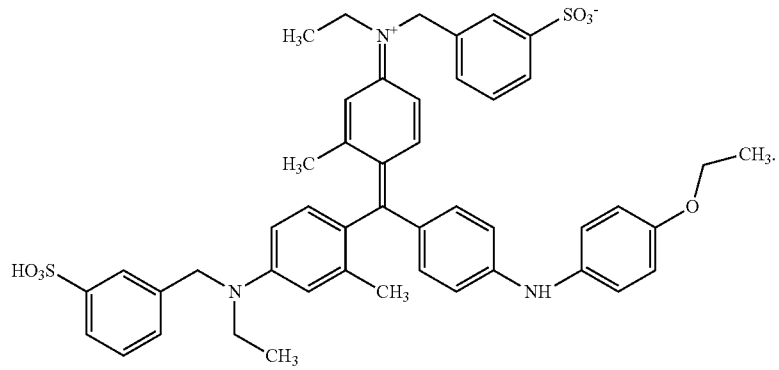

Coomassie Brilliant Blue G-250, C.I. 42655, CAS-# 6104-58-1 providing a sample comprising a protein;
providing a reagent comprising a dye corresponding in structure to a following formula:

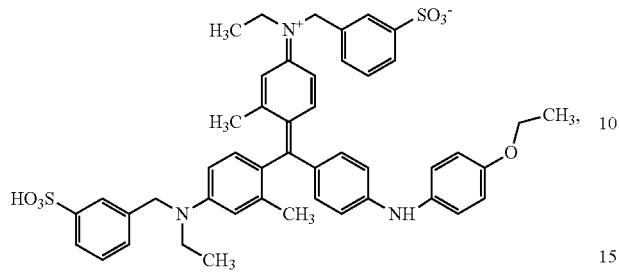

wherein a pH-value of the reagent is about pH 0.85 to pH 1.1;
combining the sample and the reagent to form a mixture; and
determining the amount of the protein in the sample by:
measuring a first absorption value of the mixture at a first wavelength of about 580 to 620 nm;
measuring a second absorption value of the mixture at a second wavelength of about 520 to 370 nm; and
determining a ratio of the first absorption value to the second absorption value, which is used for determining the amount of the protein.

2. The method of claim 1, wherein the pH-value of the reagent is about pH 0.90 to pH 1.05.

3. The method of claim 1, wherein the pH-value of the reagent is about pH 0.95 to pH 1.00.

4. The method of claim 1, wherein the first wavelength is about 590 to about 600 nm and the second wavelength is about 470 to about 400 nm.

5. The method of claim 1, wherein the first wavelength is about 595 nm and the second wavelength is about 470 nm.

6. The method of claim 1, wherein the dye is used in an acid medium wherein the acid has a pKa-value from 1 to 2.

7. The method of claim 1, wherein a concentration of the dye in the reagent is from 0.001% to 0.1% (w/v).

8. The method of claim 1, wherein an alcohol is added to the reagent.

9. The method of claim 8, wherein the alcohol is selected from one or more alcohols of the group consisting of methanol, ethanol and propanol.

10. The method of claim 8, wherein an alcohol concentration in the reagent is from 0.1% to 10% (w/v).

11. The method of claim 1, wherein the protein-containing sample is urine, serum, cerebrospinal fluid, food, or any other biologically derived fluid or extract.

* * * * *